United States Patent
Lattner et al.

(10) Patent No.: US 12,083,171 B2
(45) Date of Patent: Sep. 10, 2024

(54) C1-ESTERASE INHIBITOR PREPARATION

(71) Applicant: OCTAPHARMA AG, Lachen (CH)

(72) Inventors: Georg Lattner, Vienna (AT); Klaus Tschetschkowitsch, Vienna (AT); Almira Dugic, Vienna (AT)

(73) Assignee: OCTAPHARMA AG, Lachen (CH)

( * ) Notice: Subject to any disclaimer, the term of this patent is extended or adjusted under 35 U.S.C. 154(b) by 542 days.

(21) Appl. No.: 16/613,521

(22) PCT Filed: May 16, 2018

(86) PCT No.: PCT/EP2018/062766
§ 371 (c)(1),
(2) Date: Nov. 14, 2019

(87) PCT Pub. No.: WO2018/210944
PCT Pub. Date: Nov. 22, 2018

(65) Prior Publication Data
US 2020/0069780 A1 Mar. 5, 2020

(30) Foreign Application Priority Data
May 16, 2017 (EP) ..................... 17171352

(51) Int. Cl.
*A61K 38/57* (2006.01)
*A61K 9/00* (2006.01)
*A61K 9/08* (2006.01)
*A61K 9/19* (2006.01)
*A61K 47/18* (2017.01)

(52) U.S. Cl.
CPC ............ *A61K 38/57* (2013.01); *A61K 9/0029* (2013.01); *A61K 9/08* (2013.01); *A61K 9/19* (2013.01); *A61K 47/183* (2013.01)

(58) Field of Classification Search
None
See application file for complete search history.

(56) References Cited

U.S. PATENT DOCUMENTS

| 5,681,750 | A | 10/1997 | Poulle et al. |
| 2003/0140358 | A1 | 7/2003 | Nuijens et al. |
| 2020/0069780 | A1* | 3/2020 | Lattner .................. A61K 9/08 |

FOREIGN PATENT DOCUMENTS

| WO | 2009/073569 | 6/2009 |
| WO | 2016/131958 | 8/2016 |

OTHER PUBLICATIONS

International Search Report and Written Opinion of the International Searching Authority, issued Jul. 31, 2018 in corresponding International Patent Application No. PCT/EP2018/062766.
Agostoni et al., "Hereditary and acquired angioedema: Problems and progress: Proceedings of the third C1 esterase inhibitor deficiency workshop and beyond", Supplement to the Journal of Allergy and Clinical Immunology, 114(3): S51-S131 (2004).

* cited by examiner

*Primary Examiner* — Hope A Robinson
(74) *Attorney, Agent, or Firm* — Wenderoth, Lind & Ponack, L.L.P.

(57) ABSTRACT

The present invention relates to a stable C1-esterase-inhibitor (C1-Inh) preparation, which is liquid or lyophilised, characterised by a histidine content of 5-400 mM but does not contain citrate or phosphate. It further relates to a kit including the C1-Inh preparation.

26 Claims, 2 Drawing Sheets

C1-ESTERASE INHIBITOR PREPARATION

TECHNICAL FIELD OF THE INVENTION

The present invention relates to a formulation of a high purity C1-Inh preparation and a purification process to obtain the high purity C1-esterase-inhibitor (C1-Inh or C1I) from a C1-Inh containing source.

BACKGROUND OF THE INVENTION

C1-esterase-inhibitor is a single-chain glycoprotein with 478 amino acid residues and an apparent monomolecular weight of approximately 106 kDa measured by SDS electrophoresis. It is mainly produced in the liver and is present in normal human plasma at concentrations of about 0.14-0.38 mg/ml, which is equivalent to 1 unit/ml plasma [*Production of Plasma Proteins for Therapeutic Use*, First Edition, 241-258, Edited by Joseph Bertolini, Neil Goss and John Curling, 2013 John Wiley & Sons].

A qualitative or quantitative deficiency of C1-Inh is known to be the fundamental cause of hereditary or congenital angioedema (HAE), which is an inherited and rare disease, manifesting itself as swelling of the dermis, subcutaneous tissue, mucosa and submucosal tissues. Angioedema is a potentially life threatening disease, as trachea or air tube obstruction and finally suffocation may occur.

One possible treatment route is replacement of malfunctioning or missing protein with functional C1-esterase-inhibitor either during an acute attack or as a lifelong prophylactic treatment. In either case it is advisable to administer a C1-Inh concentrate of highest possible purity in order to omit the development of adverse effects, such as development of antibodies directed against C1-Inh. The product of choice should thus be practically free of any other proteins as well as of aggregates of C1-Inh or degraded or dysfunctional C1-Inh to facilitate in particular lifelong prophylactic treatment without antibody development or other adverse event. In cases of acute attacks with trachea obstruction administration of C1-Inh preparations at the earliest possible stage is medically indicated to avoid possible suffocation.

Said deficiencies can be corrected by replacement therapy with intravenous or subcutaneous injection of C1-Inh preparations of blood plasma or recombinant origin. However, treatments are afflicted with the risk of introduction of pathogens, e.g. viruses, into a patient and are thereby generating additional disorders. It is thus advisable to apply only C1-Inh compositions to restore C1-Inh at physiological levels, which have undergone pathogen reduction steps during manufacturing comprising reduction and inactivation steps.

While C1-Inh concentrates of high purity and low content of aggregates are known these preparations suffer from being unstable in liquid form, in particular. Consequently, stable C1-Inh preparations were only known as lyophilised products with the drawback of losing valuable time during reconstitution for treatment of acute attacks affecting the trachea, thus endangering a patient's life during an acute HAE attack.

Various processes for purification of C1-Inh incorporating in most cases at least one precipitation and several chromatographic steps have been described during the last few decades.

Sim and Reboul describe such a process. Polyethylene glycol (PEG) precipitation is performed on blood plasma followed by anion-exchange chromatography (AEX) with a DEAE resin and chromatography with a Concanavalin-A resin. The obtained product displayed a purity of more than 95% on SDS-page gel with at least 2 impurities of 60 kDa and 30 kDa.

Prograis et al. describe a purification process for C1-Inh starting with PEG fractionation of human plasma, followed by AEX-chromatography on a DEAE resin and metal-chelate chromatography. Finally the process included an immune-adsorption chromatography. C1-Inh was kept in phosphate buffered sodium chloride (PBS) and showed a slight impurity of about 93 kDa on SDS-PAGE under non-reducing conditions.

Teh and Froger disclose purification of C1-Inh by batch adsorption of cryosupernatant with a DEAE resin succeeded by PEG precipitation and cation-exchange chromatography on a CM resin. The lyophilised and heat treated product displayed a purity of more than 95% on a SDS-PAGE gel with only one visible band.

U.S. Pat. No. 4,915,945 relates to a process for the purification of C1 inactivator which comprises batch adsorption of cryosupernatant with a DEAE resin followed by batch adsorption of the supernatant of the DEAE adsorption step with a QAE resin. The C1-Inh is eluted from the QAE resin and precipitated by ammonium sulphate and the redissolved precipitate subjected to hydrophobic interaction chromatography (HIC) over Phenyl-Sepharose®.

The purification process of U.S. Pat. No. 5,030,578 consists of PEG fractionation of blood plasma, chromatography over jacalin-agarose and HIC over Phenyl-Sepharose®. The product is said to be without any traces of contaminants according to SDS-PAGE and is formulated with PBS.

WO-A2-01/46219 relates to a method for production of a C1-Inh containing composition, which includes binding of C1-Inh on a first anion-exchange resin, elution of bound C1-Inh and PEG precipitation, wherein the C1-Inh remains in the supernatant. The supernatant of the PEG precipitation is treated with S/D reagents for virus inactivation and C1-Inh is then bound to a second anion exchange resin. The C1-Inh containing eluate of the second anion-exchange resin is later subjected to nanofiltration and after exchanging to a sodium citrate-trehalose-sodium chloride buffer lyophilised. The obtained product displayed a specific activity of about 6 units/mg protein and an antigen/activity ratio of about 1.1/1.

Kumar et al. described a purification process consisting of 3 chromatographic steps to obtain high purity C1-Inh. The first step captures C1-Inh from human plasma with a DEAE resin and is succeeded by HIC on a phenyl resin and a polishing step comprising cation exchange chromatography (CEX) on a TMAE resin. Finally the buffer was exchanged to a 10 mM sodium citrate, 0.13 M glycine and 0.14 M sodium buffer at pH=6.8. The purity was determined to be 98-99% by SDS-PAGE, SEC, and RP-HPLC.

Feussner et al. disclosed a biochemical comparison of four commercially available C1-Inh concentrates. The concentrates are Berinert®, Ruconest®, Cinryze® and Cetor® of which Ruconest® is of transgenic origin whereas the remaining 3 concentrates are plasma derived products. All preparations are only available as lyophilised products.

WO-A2-2014/145519 relates to C1-Inh compositions formulated with citrate, phosphate, histidine or Tris at various pH values. Histidine formulated compositions experienced a reduction of monomer content of about 30% within 2 weeks storage at 25° C.

So far it was not possible to satisfy the requirements of high purity for long term treatment, compatibility with human glycosylation and the necessity of a liquid and stable product in order to avoid antibody development, provide highest compatibility with humans and have a liquid product for immediate use, if necessary.

SUMMARY OF THE INVENTION

The present invention is based on the surprising finding that histidine sufficiently stabilizes C1-Inh in liquid and lyophilized compositions.

Thus, according a first aspect, the invention provides a C1-esterase-inhibitor (C1-Inh) preparation, wherein the C1-Inh preparation contains histidine content in a concentration in the range of 5 to 400 mM but does not contain citrate or phosphate.

The C1-Inh according to the invention is in particular a C1-Inh from a naturally source, such as blood and obtained by a purification comprising batch adsorption of cryo-poor-plasma on a quaternary-amino-ethyl (QAE) resin, solvent/detergent (S/D) treatment of the QAE eluate for virus inactivation, anion-exchange chromatography on a diethyl-amino-ethyl (DEAE) resin succeeded by a polyethylene-glycol (PEG) precipitation, cation-exchange chromatography on a carboxy-methyl (CM) resin and a polishing hydrophobic interaction chromatography (HIC). The resulting intermediate solution is nanofiltered for pathogen removal and formulated with histidine and eventually at least one additional amino acid selected from arginine and glycine. The final product is stable either as a liquid at 1° C. to 8° C. or lyophilised up to room temperature.

This combination of process steps leads to human blood plasma derived C1-Inh compositions of sufficiently high purity, determined by size exclusion high pressure liquid chromatography (SE-HPLC or SEC). The C1-Inh compositions of the present invention are stable enough for long term storage. This means that the generation of C1-Inh fragments is minimized and the C1-Inh monomer molecules have a low tendency to form polymers.

According to a second aspect, the invention provides a kit consisting of a first receptacle containing the C1-Inh preparation according to the first aspect, a second receptacle containing water for injection, and a transfer set enabling reconstitution of the lyophilisate in a sterile manner, wherein the C1-Inh preparation is lyophilised.

According to a third aspect, the invention provides a kit consisting of a syringe prefilled with the C1-Inh preparation according to the first aspect, wherein the C1-Inh preparation is liquid and wherein the preparation is stable for at least 12 months when being stored at 1-8° C., in particular for at least 24 months at 1-8° C.

According to a fourth aspect, the invention provides a kit consisting of a syringe prefilled with the C1-Inh preparation according to the first aspect, wherein the C1-Inh preparation is liquid and wherein the preparation is stable for at least 12 months when being stored at 1-8° C., in particular for at least 24 months at 1-8° C.

According to a fifth aspect, the invention relates to the use of histidine for the stabilization of C1-Inh, wherein the histidine is added to the formulation buffer of C1-Inh and wherein the concentration of histidine is in the range from 5 to 400 mM.

According to a sixth aspect, the invention relates to the use of histidine for increasing the bioavailability of subcutaneously administered C1-Inh, wherein the histidine is added to the formulation buffer of C1-Inh before administration and wherein the concentration of histidine is in the range from 5 to 400 mM.

DETAILED DESCRIPTION

Figure 1:
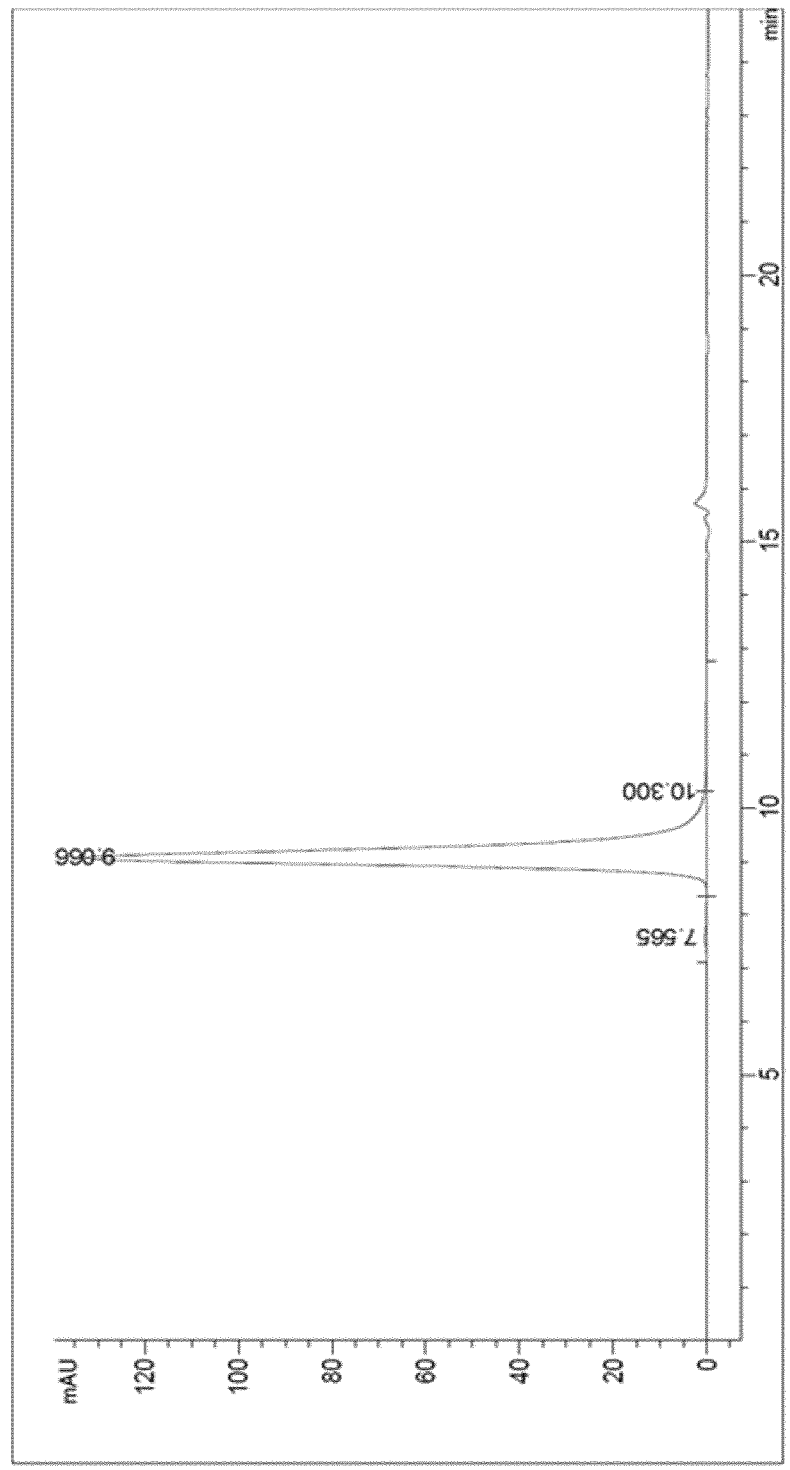
FIG. 1 depicts a typical SEC chromatogram of a C1-Inh composition obtained by the process described below and used as starting material for stability studies. The monomolecular signal has its maximum at 9.069 minutes and also two non-monomolecular weight fractions at 7.565 and 11.625 minutes were integrated. The area under the curve (AUC) of the monomolecular signal represents 99.38% of the total AUC.
Figure 2:
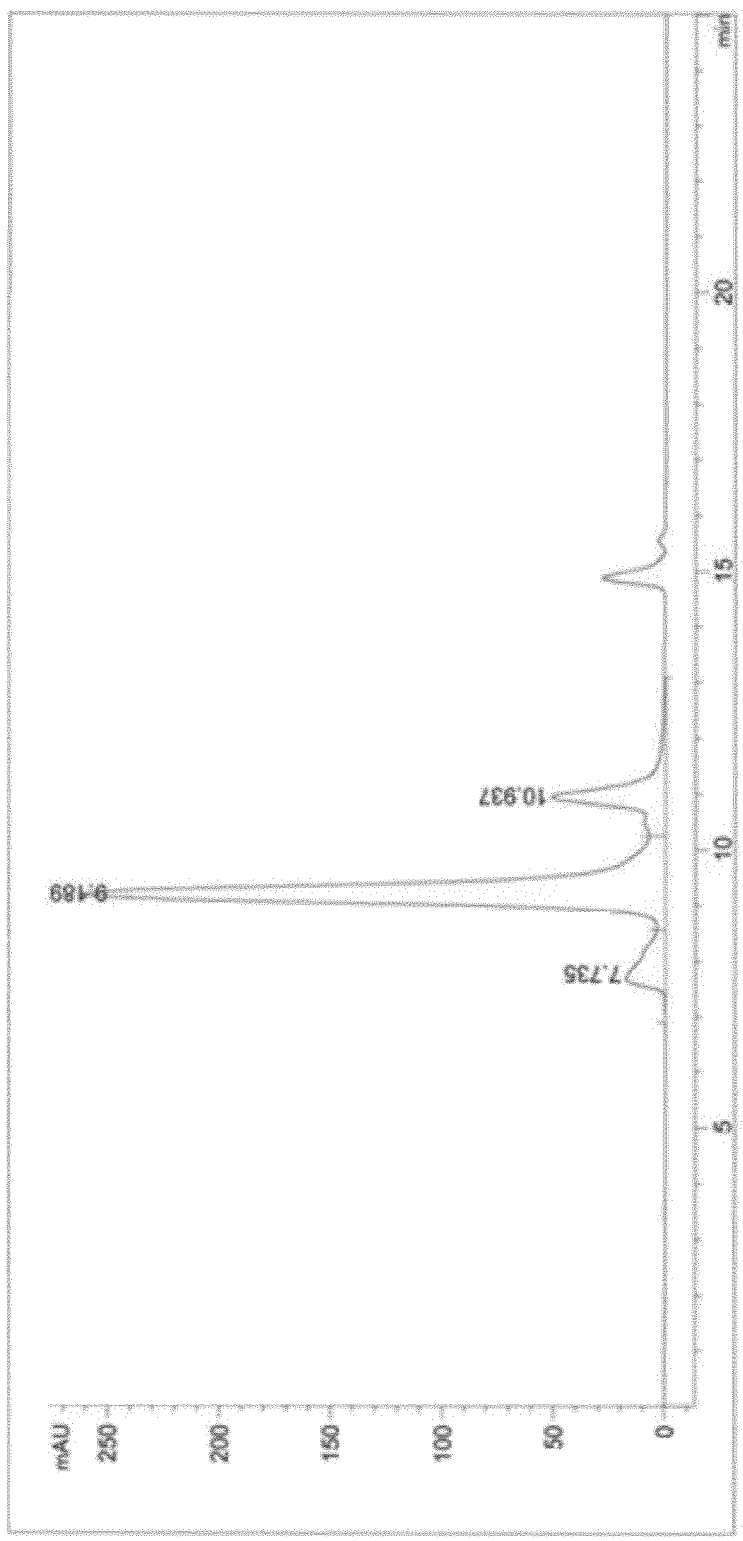
FIG. 2 depicts a typical SEC chromatogram of a C1-Inh composition containing larger quantities of non-monomolecular weight fraction. The monomolecular signal is also dominating but its AUC is just 75.38%. The two non-monomolecular weight fractions at 7.735 and 10.937 minutes are clearly visible. Such preparations were not obtained by the process described below and not used in a stability study. The purpose of FIG. 2 is just for illustration of typical non-monomolecular weight fractions. Signals visible at about 15 to 16 minutes are caused by the solvent front generated in the SEC method and are thus not considered for quantification.

According to a first aspect, the present invention provides a stable preparation comprising C1-Inh of high purity in a formulation with the amino acid histidine. The inventors surprisingly found that histidine already at low concentrations is able to provide stability, in particular storage stability, to C1-Inh preparations. Specifically, histidine concentrations as low as 5 mM are able to stabilize the C1-Inh in the preparations. Thus, the concentration of histidine is at least 5 mM.

As used herein the term "histidine" refers to the proteinogenic L-histidine. The histidine may be added to the C1-Inh preparation in pure form, in form of monohydrochloride, a monohydrate or in form of a salt, other than monohydrochloride. The lower limit of the histidine concentration may be 6 mM, 7 mM, 8 mM, 9 mM, 10 mM, 11 mM, 12 mM, 13 mM, 14 mM, or 15 mM.

As shown in the Examples, concentrations of histidine of 15 mM and 30 mM have a strong effect in the stabilization of the C1-Inh preparation. Thus, according to a preferred embodiment the lower limit of the histidine concentration is 8 mM. More preferably, the lower limit of the histidine concentration is 10 mM. Most preferably, the lower limit of the histidine concentration is 15 mM.

In principle, with respect to the stabilizing property, there should be no upper limit. For practical reasons and in particular considering the osmolality of the preparation, a concentration of 400 mM appears to be a reasonable upper limit. Thus, according to one embodiment, the histidine concentration of the C1-Inh preparation is 400 mM or less.

Accordingly, the histidine concentration may be, for example, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM 15 mM, 20 mM, 25 mM, 30 mM, 35 mM, 40 mM, 45 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 310 mM, 320 mM, 330 mM, 340 mM, 350 mM, 360 mM, 370 mM, 380 mM, 390 mM, or 400 mM.

As shown in the examples 200 mM histidine is able to stabilize C1-Inh preparations with C1-Inh concentrations of 500 IIi/mi. According to a further embodiment, the histidine concentration is 300 mM or less. According to a further embodiment, the concentration is 250 mM or less. The histidine concentration may also be 200 mM or less.

According to one embodiment, the histidine concentration is in the range of 5 to 400 mM. According to a further embodiment, the histidine concentration is in the range of 8 to 300 mM. According to a further embodiment, the histidine concentration is in the range of 10 to 250 mM. According to a further embodiment, the histidine concentration is in the range of 12 to 200 mM. According to a further embodiment, the histidine concentration is in the range of 14 to 150 mM.

The term "high purity" in the sense of the invention defines a protein composition with C1-Inh from a natural source, in particular human blood or a fraction thereof, as the main component, wherein the percentage of other protein components is below 2 wt.-%. Moreover, in a high purity C1-Inh composition, the C1-Inh is almost exclusively in the monomeric state, i.e. the NMF is below 2 wt.-%.

Due to the stabilizing effect of histidine the C1-Inh preparation of the present invention does not require buffer components generally used for C1-Inh such as phosphate buffer or citrate buffer. Citrate buffers have the disadvantage that they may cause local irritations when administered to a patient.

Accordingly, in the C1-Inh preparation of the invention preferably phosphate or citrate buffers are absent. More preferably, both, phosphate and citrate buffers are absent.

The C1-Inh preparation may be in liquid state or lyophilised. A preferred embodiment of the first aspect is a stable C1-Inh preparation, which is stable for at least 24 months at 1° C. to 30° C., in particular at 1° C. to 25° C.

According to one embodiment is the preparation comprises C1-Inh of high purity at a concentration of 50 to 2500 IU/ml, such as at a concentration of 50 IU/ml, 60 IU/ml, 70 IU/ml, 80 IU/ml, 90 IU/ml, 100 IU/ml, 150 IU/ml, 200 IU/ml, 250 IU/ml, 300 IU/ml, 350 IU/ml, 400 IU/ml, 450 IU/ml, 500 IU/, 550 IU/ml, 600 IU/ml, 650 IU/ml, 700 IU/ml, 750 IU/ml, 800 IU/ml, 850 IU/ml, 900 IU/ml, 950 IU/ml, 10000 IU/ml, 1100 IU/ml, 1200 IU/ml, 1300 IU/ml, 1400 IU/ml, 1500 IU/ml, 1600 IU/ml, 1700 IU/ml, 1800 IU/ml, 1900 IU/ml, 2000 IU/ml, 2100 IU/ml, 2200 IU/ml, 2300 IU/ml, 2400 IU/ml, or 2500 IIi/mi. Preferably, the C1-Inh concentration is in the range from 100 to 1500 IU/ml, more preferably in the range from 150 to 1000 IIi/mi. In case of a lyophilised C1-Inh preparation, in the context of this application, the concentration of C1-Inh is defined as concentration after reconstitution.

A C1-Inh product with the required purity is obtainable by the following process. In order to obtain the human blood plasma derived C1-Inh compositions of sufficiently high purity the following purification process may be applied.

Heparin is added to cooled Cryo-poor-plasma. After capture by QAE resin and subsequently elution a virus inactivation step is performed with a combination of a solvent and a detergent (S/D treatment). The S/D treated solution is afterwards diluted with water.

This diluted solution is subsequently subjected to an anion exchange chromatography, in which the C1-Inh is bound to the resin and then eluted with NaCl in a buffered solution. The obtained eluate is cooled to 5° C.±4° C. before starting the PEG precipitation.

A PEG-4000 solution of about 60% is mixed with the eluate to precipitate unwanted proteins. After removal of the precipitate, e.g. by depth filtration, the obtained C1-Inh filtrate is mixed with solid PEG to precipitate C1-Inh. The solid particles are separated from the liquid, e.g. by depth filtration, and the obtained paste, which might be stored frozen, is kept for further processing as it contains C1-Inh.

The C1-Inh paste is solubilised in a buffer at pH=6.0±0.2 and the obtained solution is afterwards clarified. The clarified solution is subjected to cation-exchange chromatography. Impurities are washed off from the loaded resin and C1-Inh is then eluted in a purity >90%.

HIC chromatography is performed with the cation-exchange eluate to obtain a purity of >99% C1-Inh. The C1-Inh is bound to the resin and by decreasing the ionic strength eluted in pure form without polymers and impurities, which is demonstrated by a SEC AUC of <1% different from the monomeric peak. The buffer is exchanged by an ultra-/diafiltration (UDF) with a 10 kDa membrane against a buffer containing histidine, sodium chloride and amino acids. The obtained buffer exchanged C1-Inh eluate is prefiltered and subsequently subjected to nanofiltration for pathogen removal. The nanofiltrate obtained is thereafter subjected to another UDF with a 10 kDa membrane to be concentrated to the desired C1-Inh concentration and formulated with the desired excipients.

Alternatively the C1-Inh product can be obtained by processes known from prior-art, such as Kumar et al.

It was surprisingly found that it is not necessary for lyophilised preparations of the present invention to add bulking agents to obtain a lyophilisation cake allowing fast reconstitution.

The C1-Inh preparation according to the first aspect may comprise further naturally occurring amino acids in addition to histidine.

For example, the C1-Inh preparation may comprise one, two, three, four, five or six further naturally occurring amino acids. According to one embodiment of the first aspect, the C1-Inh preparation comprises one or two further amino acids selected from arginine and glycine.

As used herein the term "arginine" refers to the proteinogenic L-arginine. The arginine may be added to the C1-Inh preparation in pure form, in form of monohydrochloride, a monohydrate or in form of a salt other than monohydrochloride. The glycine may added to the C1-Inh preparation in pure form, in form of monohydrochloride, a monohydrate or in form of a salt. Arginine may be present in a concentration in the range of 5 to 400 mM. The arginine concentration may be 5 mM, 6 mM, 7 mM, 8 mM, 9 mM, 10 mM, 15 mM, 20 mM, 25 mM, 30 mM, 35 mM, 40 mM, 45 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 310 mM, 320 mM, 330 mM, 340 mM, 350 mM, 360 mM, 370 mM, 380 mM, 390 mM, or 400 mM.

According to a one embodiment of the first aspect, the arginine concentration is in the range of 10 to 300 mM. According to a further embodiment, the arginine concentration is in the range of 20 to 250 mM. According to a further embodiment, the arginine concentration is in the range of 30 to 150 mM. According to a further embodiment, the arginine concentration is in the range of 50 to 100 mM.

Glycine may be present in a concentration in the range of 2 to 200 mM. The glycine concentration in the C1-Inh preparation may be 2 mM, 3 mM, 4, mM, 5 mM, 6 mM, 7 mM, 8 mM, 9 mM, 10 mM, 15 mM, 20 mM, 25 mM, 30 mM, 35 mM, 40 mM, 45 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM.

According to a one embodiment of the first aspect, the glycine concentration is in the range of 5 to 200 mM. According to a further embodiment, the glycine concentration is in the range of 7 to 150 mM. According to a further embodiment, the glycine concentration is in the range of 8 to 80 mM. According to a further embodiment, the glycine concentration is in the range of 9 to 60 mM.

According to one embodiment, the C1-Inh preparation contains both arginine and glycine. According to a further embodiment, the arginine concentration is in the range of 50 to 100 mM and the glycine concentration is in the range of 9 to 60 mM.

From the experiments, it appears that, without wanting to be bound by theory that in addition to presence of histidine the osmolality is important for the stability of C1-Inh. According to one embodiment of the first aspect, the osmolality of the C1-Inh preparation is in the range from 200 to 800 mOsmol/kg. According to a further embodiment, the osmolality is in the range of 200 to 600 mOsmol/kg. According to a further embodiment, the osmolality is in the range of 250 to 500 mOsmol/kg.

To achieve the osmolality the total concentration of amino acids is preferably in the range 50 to 600 mM. According to a further embodiment, the total concentration of amino acids is in the range of 80 to 400 mM. According to a further embodiment, the total concentration of amino acids is is in the range of 90 to 350 mM. According to a further embodiment, the total concentration of amino acids is in the range of 100 to 280 mM.

The C1-Inh preparation according to the invention may further comprise a salt. The salt is preferably selected from the group consisting of NaCl, NaSO$_4$, MgSO$_4$, MgCl$_2$, CaCl$_2$ and KCl or mixture thereof.

The salt may be present in a concentration in the range of 5 to 200 mM. The salt concentration in the C1-Inh preparation may be 5 mM, 6 mM, 7 mM, 8 mM, 9 mM, 10 mM, 15 mM, 20 mM, 25 mM, 30 mM, 35 mM, 40 mM, 45 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM.

According to one embodiment, the salt concentration is in the range of 8 to 150 mM. According to a further embodiment, the salt concentration is in the range of 10 to 100 mM. According to a further embodiment, the salt concentration is in the range of 15 to 80 mM. According to a further embodiment, the salt concentration is in the range of 20 to 60 mM.

According to one embodiment of the first aspect, the salt is sodium chloride (NaCl). Accordingly, the C1-Inh preparation may comprise glycine and sodium chloride. Alternatively, the C1-Inh preparation may comprise arginine and sodium chloride. According to one embodiment, the C1-Inh preparation comprises arginine and sodium chloride.

In the lyophilised state, the C1-Inh preparation according to the first aspect is stable for at least 18 months at 1° C. to 30° C., in particular at 1° C. to 25° C., wherein the preparation does not contain citrate or phosphate. The demanded properties are obtained by the formulations of the present invention in combination with C1-Inh purities obtainable by the process described above or by other processes known from prior-art, such as Kumar et al.

A further preferred embodiment of the first aspect is the C1-Inh preparation in a lyophilized state comprising C1-Inh of high purity at a concentration of 50 to 2500 IU/ml after reconstitution, in particular 100 to 1500 IU/ml, preferably 150 to 1000 IU/ml, which is suitable for subcutaneous or intravenous application, is formulated with histidine and one or two additional amino acids selected from arginine and glycine.

A further preferred embodiment of the first aspect is the lyophilized preparation comprising C1-Inh of high purity in a formulation buffer containing histidine, sodium chloride and one or a second additional amino acid selected from glycine and arginine, wherein the preparation has an osmolality of 200-800 mOsmol/kg and a pH value of 6.0 to 8.0, in particular a pH value in the range of 7.0 to 7.8, preferably a pH value of 7.1 to 7.5.

A further preferred embodiment of the first aspect is the lyophilized preparation comprising C1-Inh of high purity in a formulation buffer containing histidine, sodium chloride and arginine, wherein the preparation has an osmolality of 200-800 mOsmol/kg, in particular of 250-500 mOsmol/kg, and a pH value of 6.0 to 8.0, in particular a pH value in the range of 7.0 to 7.8, preferably a pH value of 7.1 to 7.5.

A further preferred embodiment of the first aspect is the lyophilized C1-Inh preparation comprising a formulation buffer consisting of 10-100 mM sodium chloride, 5-400 mM histidine and 5-400 mM arginine, characterised by an osmolality of 200-800 mOsmol/kg, in particular of 250-500 mOsmol/kg, and a pH value of 6.0 to 8.0, in particular by a pH value in the range of 7.0 to 7.8, preferably a pH value of 7.1 to 7.5.

A further preferred embodiment of the first aspect is the lyophilized C1-Inh preparation containing 200±50 IU/ml C1-Inh, 25-35 mM sodium chloride, 10-20 mM histidine and 70-90 mM arginine, in particular about 16 mM histidine, about 80 mM arginine, about 40 mM glycine and about 31 mM NaCl, which is adjusted to a pH of 7.1 to 7.5.

A further preferred embodiment of the first aspect is the lyophilized C1-Inh preparation containing 500±125 IU/ml C1-Inh, 25-35 mM sodium chloride, 10-20 mM histidine and 70-90 mM arginine, in particular about 16 mM histidine, about 80 mM arginine, about 40 mM glycine and about 31 mM NaCl, which is adjusted to a pH of 7.1 to 7.5.

A further preferred embodiment of the first aspect is lyophilized C1-Inh preparation containing 1000±250 IU/ml C1-Inh, 25-35 mM sodium chloride, 10-20 mM histidine and 70-90 mM arginine, in particular about 16 mM histidine, about 80 mM arginine, about 40 mM glycine and about 31 mM NaCl, which is adjusted to a pH of 7.1 to 7.5.

According to one embodiment of the first aspect, the preparation comprising C1-Inh of high purity is a liquid preparation and stable for at least 12 months at 1° C. to 8° C., in particular for at least 24 months at 1° C. to 8° C., wherein the preparation does not contain citrate or phosphate. The demanded properties are obtained by the formulations of the present invention in combination with C1-Inh purities obtainable by the process described above or by other processes known from prior-art, such as Kumar et al.

A preferred embodiment of the first aspect of the present invention is the liquid C1-Inh preparation, which is stable for at least one month at room temperature, in particular at temperatures up to 25° C. Such a preparation can conveniently be taken on short journeys or can be carried by a patient for 24 hours a day as a possible immediate emergency treatment.

A further preferred embodiment of the first aspect of the present invention is the liquid C1-Inh, which is stable for at least one month at room temperature, in particular at temperatures up to 25° C., after it had been stored for up to 13 months at 1-8° C.

A further preferred embodiment of the first aspect is the liquid C1-Inh preparation comprising C1-Inh of high purity at a concentration of 50 to 2500 IU/ml, in particular 100 to 1500 IU/ml, preferably 150 to 1000 IU/ml, which is suitable for subcutaneous or intravenous application, is formulated with histidine and one or two additional amino acids selected from arginine and glycine.

A further preferred embodiment of the first aspect is the liquid C1-Inh preparation in a formulation buffer containing histidine, sodium chloride and one or a second additional amino acid selected from glycine and arginine, wherein the preparation has an osmolality of 200-800 mOsmol/kg, in particular of 250-500 mOsmol/kg, and a pH value of 6.0 to 8.0, in particular a pH value in the range of 7.0 to 7.8, preferably a pH value of 7.1 to 7.5.

A further preferred embodiment of the first aspect is the liquid C1-Inh preparation in a formulation buffer comprising histidine, sodium chloride and arginine, wherein the preparation has an osmolality of 200-800 mOsmol/kg, in particular of 250-500 mOsmol/kg, and a pH value of 6.0 to 8.0, in particular a pH value in the range of 7.0 to 7.8, preferably a pH value of 7.1 to 7.5.

A further preferred embodiment of the first aspect is the liquid preparation comprising C1-Inh of high purity in a formulation buffer consisting of 10-100 mM sodium chloride, 5-400 mM histidine and 5-400 mM arginine, characterised by an osmolality of 200-800 mOsmol/kg, in particular of 250-500 mOsmol/kg, and a pH value of 6.0 to 8.0, in particular by a pH value in the range of 7.0 to 7.8, preferably a pH value of 7.1 to 7.5. A further preferred embodiment of the second aspect is the liquid C1-Inh preparation in a formulation buffer consisting of 10-100 mM sodium chloride, 10-100 mM histidine and 30-200 mM arginine, characterised by an osmolality of 200-800 mOsmol/kg, in particular of 250-500 mOsmol/kg, and a pH value of 6.0 to 8.0, in particular by a pH value in the range of 7.0 to 7.8, preferably a pH value of 7.1 to 7.5.

A further preferred embodiment of the second aspect is the liquid C1-Inh preparation in a formulation buffer consisting of 20-50 mM sodium chloride, 10-50 mM histidine and 50-150 mM arginine, characterised by an osmolality of 200-800 mOsmol/kg, in particular of 250-500 mOsmol/kg, and a pH value of 6.0 to 8.0, in particular by a pH value in the range of 7.0 to 7.8, preferably a pH value of 7.1 to 7.5.

A further preferred embodiment of the first aspect the liquid C1-Inh preparation comprising 25-40 mM sodium chloride, 100-140 mM histidine, 90-130 mM arginine and 5-30 mM glycine, characterised by an osmolality of 380-500 mOsmol/kg, and a pH value of 6.0 to 8.0, in particular by a pH value in the range of 7.0 to 7.8, preferably a pH value of 7.1 to 7.5.

A further preferred embodiment of the first aspect is a liquid C1-Inh preparation comprising 200±50 IU/ml C1-Inh, of 20-50 mM sodium chloride, 10-20 mM histidine and 70-90 mM arginine, in particular about 16 mM histidine, about 80 mM arginine, about 40 mM glycine and about 31 mM NaCl, which is adjusted to a pH of 7.1 to 7.5.

A further preferred embodiment of the first aspect is a liquid C1-Inh preparation containing 200±50 IU/ml C1-Inh, of 25-35 mM sodium chloride, 10-20 mM histidine 70-90 mM arginine and 35-65 mM glycine, in particular about 15 mM histidine, about 80 mM arginine, about 55 mM glycine and about 30 mM NaCl, which is adjusted to a pH of 7.1 to 7.5.

A further preferred embodiment of the first aspect is comprising liquid C1-Inh preparation containing 500±125 IU/ml C1-Inh, of 25-35 mM sodium chloride, 25-35 mM histidine and 100-110 mM arginine, in particular about 30 mM histidine, about 105 mM arginine and about 30 mM NaCl, which is adjusted to a pH of 7.1 to 7.5.

A further preferred embodiment of the first aspect the liquid preparation comprising C1-Inh of high purity formulated to contain 500±125 IU/ml C1-Inh, of 25-35 mM sodium chloride, 115-125 mM histidine, 105-115 mM arginine and 15-25 mM glycine, in particular about 120 mM histidine, about 110 mM arginine, about 20 mM glycine and about 33 mM NaCl, which is adjusted to a pH of 7.1 to 7.5.

A further preferred embodiment of the first aspect is the liquid C1-Inh preparation containing 1000±250 IU/ml C1-Inh, of 25-35 mM sodium chloride, 10-20 mM histidine and 70-90 mM arginine, in particular about 16 mM histidine, about 80 mM arginine, about 40 mM glycine and about 31 mM NaCl, which is adjusted to a pH of 7.1 to 7.5. The C1-Inh preparation according to the first aspect is in particular useful for the treatment of hereditary or congenital angioedema (HAE).

Thus according to a second aspect, the invention provides a C1-Inh preparation for use in the treatment of hereditary or congenital angioedema (HAE), wherein the C1-Inh preparation is defined according to the first aspect.

The C1-Inh preparation may be administered in particular parenterally such as by intravenous, intramuscular or subcutaneous administration. According to one embodiment of the second aspect, the use is characterized by a subcutaneous administration of the C1-Inh preparation.

The inventors additionally showed that C1-Inh compositions formulated with histidine have a high bioavailability when administered subcutaneously. According to one embodiment the C1-Inh preparation according to the invention has a bioavailability of more than 60%, preferably more than 70%, more preferably of more than 80%, most preferably of more than 90%, when being administered subcutaneously of the bioavailability as compared to an intravenously administered C1-Inh at the same dose. The high bioavailability of the C1-Inh preparation when administered subcutaneously is shown in Table 8.

Specifically, as confirmed by the experimental results shown in Table 8, high histidine concentrations lead to particularly high bioavailabilities of C1-Inh in subcutaneous administration of the C1-Inh preparation according to the invention, in particular at high concentrations of C1-Inh of about 500 IU/ml. Accordingly, C1-Inh preparations with the concentration of C1-Inh of more than 300 IU/ml, In particular, 300 IU/ml to 1000 IU/ml The histidine concentration is preferably in the range of 50 mM to 400 mM, more preferably the range of 70 to 300 mM. According to a further embodiment, the histidine concentration is in the range of 80 to 200 mM. According to a further embodiment, the histidine concentration is in the range of 100 to 150 mM. According to a further embodiment, the histidine concentration is in the range of 110 to 130 mM.

According to a third aspect the invention provides a kit consisting of a first receptacle containing the C1-Inh preparation according to the first aspect, a second receptacle containing water for injection and a transfer set enabling reconstitution of the lyophilisate in a sterile manner. The reconstituted C1-Inh preparation may be stored up to one month prior to application at room temperature of up to 20-25° C.

According to a fourth aspect, the invention provides a kit consisting of a syringe prefilled with the C1-Inh preparation according to the first aspect, wherein the C1-Inh preparation is liquid and wherein the preparation is stable for at least 12 months when being stored at 1-8° C., in particular for at least 24 months at 1-8° C.

According to one embodiment of the fourth aspect, the C1-Inh preparation is stable for at least 23 months when being stored at 1-8° C. and for one additional month after warming to room temperature with the prerequisite that a room temperature of 20-25° C. is not exceeded within said additional month. A particularly positive effect of the kit according to the fourth aspect is the possibility to carry the kit unrefrigerated while being en route for immediate use in case an acute attack. Additionally, due to the stability it will still be possible to use the kit safely after for instance 2-3 weeks at room temperature for prophylactic treatment. Prophylactic treatment is usually done twice a week.

According to a further embodiment of the fourth aspect the kit consists of a device suitable for s.c. application, such as an "On-Body Injector", prefilled with the C1-Inh preparation of the first aspect wherein the C1-Inh preparation is liquid, wherein the preparation is stable for at least 23 months when being stored at 1-8° C. and for at least one additional month after warming to room temperature with the prerequisite that a room temperature of 20-25° C. is not exceeded within said additional month.

According to a fifth aspect, the invention relates to the use of histidine for the stabilization of C1-Inh, wherein the histidine is added to the formulation buffer of C1-Inh and wherein the concentration of histidine is in the range from 5 to 400 mM.

In the use according to the fifth aspect, a concentration of histidine may be used as defined for the C1-Inh preparation of the first aspect. In addition, a concentration of C1-Inh may be used as defined for the C1-Inh preparation of the first aspect. The formulation buffer of the C1-Inh may additionally contain any of the components defined for the C1-Inh preparation of the first aspect. The C1-Inh preparation that is stabilized by histidine may be liquid or lyophilized.

Moreover, the ratio between the molar concentration of histidine and the content of C1-Inh in IU/ml may be in the range from 1 (mM): 500 (IU/ml) to 8:1. Preferably, the ratio between the molar concentration of histidine and the content of C1-Inh in IU/ml is in the range from 1:50 to 4:1. More preferably, the ratio between the molar concentration of histidine and the content of C1-Inh in IU/ml is in the range from 1:20 to 1:1.

According to a sixth aspect, the invention relates to the use of histidine for increasing the bioavailability of subcutaneously administered C1-Inh, wherein the histidine is added to the formulation buffer of C1-Inh before administration and wherein the concentration of histidine is in the range from 5 to 400 mM.

In the use according to the sixth aspect, a concentration of histidine may be used as defined for the C1-Inh preparation of the first aspect. In addition, a concentration of C1-Inh may be used as defined for the C1-Inh preparation of the first aspect. The formulation buffer of the C1-Inh may additionally contain any of the components defined for the C1-Inh preparation of the first aspect. The C1-Inh preparation that is stabilized by histidine may be liquid or lyophilized.

For achieving a high bioavailability of subcutaneously administered C1-Inh, the ratio between the molar concentration of histidine and the content of C1-Inh in IU/ml may be in the range from 1 (mM): 500 (IU/ml) to 8:1. Preferably, the ratio between the molar concentration of histidine and the content of C1-Inh in IU/ml is in the range from 1:50 to 4:1. More preferably, the ratio between the molar concentration of histidine and the content of C1-Inh in IU/ml is in the range from 1:10 to 1:1.

Determination of Purity by Size-Exclusion Chromatography (SEC)

SEC is used to determine purity of the C1-Inhibitor solution. A standard HPLC system equipped with a Tosoh TSKgei®-Super SW3000 SEC column and a UV detector at 280 nm may be used. The running buffer contains 40 mM sodium phosphate and 300 mM sodium chloride at pH=6.95 and the recommended flow rate by the column manufacturer of 0.3 ml/min is used.

For evaluation of the chromatogram the areas under the curve of a product sample are integrated, summarized and individual peak areas are calculated as % of total peak area. Monomolecular C1-Inh elutes at about 9.2 minutes and signals prior or later than this dominant signal represent the non-monomeric fraction. Good results are obtained with above described settings with protein concentrations of about 5 mg/ml, an injection volume of 10 µl and integration from 2 to 13 minutes. The signal of monomolecular C1-Inh is dominant and its integration from about 8.6 to 10.3 minutes delivers good results for sufficiently pure preparations.

Determination of Bioavailability

In order to determine bioavailability of C1-Inh administered subcutaneously compared to C1-Inh administered intravenously an animal study was performed. Due to the similarity of human and porcine skin, pigs were chosen as animals. Pharmacokinetics of s.c. and i.v. administered C1-Inh was determined and bioavailability of s.c. administered C1-Inh was calculated as % of area under the curve (AUC) of i.v. administered C1-Inh of the same dose (IU/kg). C1-Inh blood levels were monitored for 168 hours after a single injection.

Definition of Stability

Stability according to the present invention relates storage stability, i.e. and in particular a low tendency to aggregate formation during storage over a defined period, in particular more than 6 months. Accordingly, a preparation is considered as "stable" it has generally a low tendency to form aggregates. The stability of a specific preparation is further dependent on the predefined time, on the storage temperature and the aggregate state.

Accordingly, a lyophilised C1-Inh preparation is considered to be stable over a defined period when the amount of the non-monomeric fraction is less than 4% after storage at a temperature of 25° C. or lower at the defined period. For example, a preparation is considered stable for at least 12 months if during storage period of 12 months at a temperature 25° C. or lower the NMF remained below 4%.

A liquid C1-Inh preparation is considered stable over a defined period when the amount of the non-monomeric fraction is less than 4% after storage at a temperature of 5° C. or lower at the defined period. For example, a liquid preparation is considered stable for at least 12 months if a during storage period of 12 months at a temperature of 5° C. the NMF remained below 4%.

A liquid C1-Inh preparation is considered stable over a defined period when the amount of the non-monomeric fraction is less than 15% after storage at a temperature of 15° C. or lower at the defined period. For example, a liquid preparation is considered stable for at least 10 months if a during storage period of 10 months at a temperature of 15° C. the NMF remained below 15%.

"Non-monomeric fraction", "non-monomolecular weight fraction" or "NMF" refers to the any component with a different molecular weight than monomeric C1-Inh, e.g. aggregated C1-Inh, C1-Inh fragment or contaminant proteins. In SEC, the NMF elutes prior or later than the dominant C1-Inh signal.

Examples

Arginine and histidine were in general used as monohydrochloride unless otherwise indicated.

Lyophilised Preparations According to the Present Invention

Preparation$_{lyo}$ 1 (P$_{lyo}$ 1) consisted of 200 IU/ml C1-Inh, 15 mM histidine, 80 mM arginine, 40 mM glycine and 30 mM NaCl adjusted to a pH of 7.3. P$_{lyo}$ 1 had a calculated osmolality of 290 mOsmol/kg.

Preparation$_{lyo}$ 2 (P$_{lyo}$ 2) consisted of 200 IU/ml C1-Inh, 50 mM histidine, 67 mM arginine and 28 mM NaCl adjusted to a pH of 7.4. P$_{lyo}$ 2 had a calculated osmolality of about 290 mOsmol/kg.

Preparation$_{lyo}$ 3 (P$_{lyo}$ 3) consisted of 200 IU/ml C1-Inh, 25 mM histidine, 66 mM arginine, 9 mM glycine and 49 mM NaCl adjusted to a pH of 7.3. P$_{lyo}$ 3 had a calculated osmolality of about 290 mOsmol/kg.

Preparation$_{lyo}$ 4 (P$_{lyo}$ 4) consisted of 200 IU/ml C1-Inh, 25 mM histidine, 100 mM arginine and 21 mM NaCl adjusted to a pH of 7.3. P$_{lyo}$ 4 had a calculated osmolality of about 290 mOsmol/kg.

Preparation$_{lyo}$ 6 (P$_{lyo}$ 6) consisted of 200 IU/ml C1-Inh, 10 mM histidine, 50 mM arginine, 80 mM glycine and 50 mM NaCl adjusted to a pH of 7.3. P$_{lyo}$ 6 had a calculated osmolality of about 300 mOsmol/kg.

Preparation$_{lyo}$ 5 (P$_{lyo}$ 5) consisted of 200 IU/ml C1-Inh, 10 mM histidine, 74 mM arginine, 9 mM glycine and 57 mM NaCl adjusted to a pH of 7.3. P$_{lyo}$ 5 had a calculated osmolality of about 290 mOsmol/kg.

Liquid Preparations According to the Present Invention

Preparation 1 (P1) consisted of 200 IU/ml C1-Inh, 15 mM histidine base, 80 mM arginine, 55 mM glycine and 30 mM NaCl adjusted to a pH of 7.4. P1 had a calculated osmolality of about 290 mOsmol/kg.

Preparation 2 (P2) consisted of 500 IU/ml C1-Inh, 30 mM histidine base, 105 mM arginine and 30 mM NaCl adjusted to a pH of 7.3. P2 had an osmolality of about 300 mOsmol/kg.

Preparation 3 (P3) consisted of 520 IU/ml C1-Inh, 120 mM histidine base, 110 mM arginine, 20 mM glycine and 33 mM NaCl adjusted to a pH of 7.3. P3 has osmolality of about 430 mOsmol/kg.

Comparative Preparations Containing the Same High Purity C1-Inh but Formulated not According to the Present Invention Lyophilised Preparations not According to the Present Invention Comparative Preparation$_{lyo}$ 1 (CP$_{lyo}$ 1) consisted of 200 IU/ml C1-Inh, 0 mM histidine (no histidine), 80 mM arginine, 40 mM glycine and 45 mM NaCl adjusted to a pH of 7.3. CP$_{lyo}$ 1 had a calculated osmolality of about 290 mOsmol/kg.

Comparative Preparation$_{lyo}$ 2 (CP$_{lyo}$ 2) consisted of 200 IU/ml C1-Inh, 0 mM histidine (no histidine), 50 mM arginine, 80 mM glycine and 50 mM NaCl adjusted to a pH of 7.3. CP$_{lyo}$ 2 had a calculated osmolality of about 280 mOsmol/kg.

Liquid Preparations not According to the Present Invention

Comparative Preparation 1 (CP 1) consisted of 200 IU/ml C1-Inh, 137 mM sodium chloride, 2.7 mM potassium chloride, 10 mM disodium hydrogen phosphate, and 1.8 mM potassium di hydrogen phosphate adjusted to a pH of 7.3. CP 1 had a calculated osmolality of about 315 mOsmol/kg.

Comparative Preparation 2 (CP 2) consisted of 200 IU/ml C1-Inh, 70.2 mM sodium chloride, 61.3 mM sucrose, 10.1 mM sodium citrate, 17.1 mM L-valine, 13.5 mM L-alanine, and 37.8 mM L-threonine adjusted to a pH of 7.0. CP 2 had a calculated osmolality of about 380 mOsmol/kg.

Results

SEC data for the non-monomeric fraction (NMF) is indicated in the tables as NMF.

Table 1 contains SEC data given in % of total area of lyophilised preparations according to the invention determined immediately after formulation ($t_o$) and after storage for some months at 25° C.

Table 2 contains SEC data given in % of total area of lyophilised preparations which are not according to the invention. SEC data was determined immediately after formulation ($t_o$) and after storage for some months at 25° C.

Table 3 contains SEC data given in % of total area of liquid preparations according to the invention determined immediately after formulation ($t_o$) and after storage for some months at 5° C.

Table 4 contains SEC data given in % of total area of liquid preparations which are not according to the invention. SEC data was determined immediately after formulation ($t_o$) and after storage for some months at 5° C.

Table 5 contains SEC data given in % of total area of liquid preparations according to the invention determined immediately after formulation ($t_o$) and after storage for some months at 15° C.

Table 6 contains SEC data given in % of total area of liquid preparations which are not according to the invention. SEC data was determined immediately after formulation ($t_o$) and after storage for some months at 15° C.

Table 7 contains SEC data given in % of total area of liquid preparations according to the invention determined immediately after formulation ($t_o$) and after storage for one month at 25° C.

Table 8 contains data related to C1-Inhibitor kinetics of preparations applied subcutaneously respectively intravenously. Data is given in % of area under the curve (AUC) of intravenously administered C1-Inhhibitor of the same dosing regimen, i.e. bioavailability.

TABLE 1

| (lyophilised, 25° C.) - values given as [%] | | | | |
|---|---|---|---|---|
| | $t_0$ | 1 month | 3 months | 6 months |
| P$_{lyo}$ 1 Monomol. C1I | 99.59 | 99.49 | 99.47 | 99.47 |
| P$_{lyo}$ 1 NMF | 0.41 | 0.51 | 0.53 | 0.53 |
| P$_{lyo}$ 2 Monomol. C1I | 99.60 | 99.58 | 99.38 | 99.33 |
| P$_{lyo}$ 2 NMF | 0.40 | 0.42 | 0.62 | 0.67 |
| P$_{lyo}$ 3 Monomol. C1I | 99.61 | 99.56 | 99.33 | 99.37 |
| P$_{lyo}$ 3 NMF | 0.39 | 0.44 | 0.67 | 0.63 |
| P$_{lyo}$ 4 Monomol. C1I | 99.61 | 99.53 | 99.48 | 99.36 |
| P$_{lyo}$ 4 NMF | 0.39 | 0.47 | 0.52 | 0.64 |
| P$_{lyo}$ 5 Monomol. C1I | 99.59 | 99.51 | 99.28 | 99.40 |

TABLE 1-continued (lyophilised, 25° C.) - values given as [%]

|  | $t_0$ | 1 month | 3 months | 6 months |
|---|---|---|---|---|
| $P_{lyo}$ 5 NMF | 0.41 | 0.49 | 0.72 | 0.60 |
| $P_{lyo}$ 6 Monomol. C1I | 99.54 | 99.47 | 99.37 | 99.17 |
| $P_{lyo}$ 6 NMF | 0.46 | 0.53 | 0.63 | 0.83 |

TABLE 2

(lyophilized, 25° C.) - values given as [%]

|  | $t_0$ | 1 month | 3 months | 6 months |
|---|---|---|---|---|
| $CP_{lyo}$ 1 Monomol. C1I | 99.58 | 99.48 | 99.25 | 99.09 |
| $CP_{lyo}$ 1 NMF | 0.42 | 0.52 | 0.75 | 0.91 |
| $CP_{lyo}$ 2 Monomol. C1I | 99.58 | 99.50 | 99.33 | 99.37 |
| $CP_{lyo}$ 2 NMF | 0.42 | 0.50 | 0.67 | 0.63 |

TABLE 3

(liquid, 5° C.) - values given as [%]

|  | $t_0$ | 1.5 month | 2 months | 4 months | 10 months | 13 months |
|---|---|---|---|---|---|---|
| P1 Monomol. C1I | 99.57 | 99.56 | 99.28 | 98.96 | 98.75 | 98.77 |
| P1 NMF | 0.43 | 0.44 | 0.72 | 1.04 | 1.25 | 1.23 |
| P2 Monomol. C1I | 99.55 | 99.59 | 99.38 | 99.24 | 99.04 | 99.00 |
| P2 NMF | 0.45 | 0.41 | 0.62 | 0.76 | 0.96 | 1.00 |

TABLE 4

(liquid, 5° C.) values given as [%]; n.d.—not determined

|  | $t_0$ | 4 months | 6 months | 9 months |
|---|---|---|---|---|
| CP1 Monomol. C1I | 98.24 | n.d. | 90.83 | 89.31 |
| CP1 NMF | 1.76 | n.d. | 9.17 | 10.69 |
| CP2 Monomol. C1I | 97.51 | n.d. | 76.57 | 80.30 |
| CP2 NMF | 2.49 | n.d. | 23.43 | 19.7 |

TABLE 5

(liquid, 15° C.) - values given as [%]

|  | $t_0$ | 1.5 months | 2 months | 4 months | 9 months | 13 months |
|---|---|---|---|---|---|---|
| P1 Monomol. C1I | 99.55 | 99.02 | 98.60 | 97.64 | 88.94 | 84.59 |
| P1 NMF | 0.45 | 0.98 | 1.40 | 2.36 | 11.06 | 15.41 |
| P2 Monomol. C1I | 99.55 | 99.11 | 98.71 | 97.85 | 89.60 | 85.48 |
| P2 NMF | 0.45 | 0.89 | 1.29 | 2.15 | 10.40 | 14.52 |

TABLE 6

(liquid, 15° C.) - values given as [%]; n.d.—not determined

|  | $t_0$ | 1.5 month | 2 months | 4 months | 9 months |
|---|---|---|---|---|---|
| CP1 Monomol. C1I | 98.24 | n.d. | n.d. | n.d. | 83.43 |
| CP1 NMF | 1.76 | n.d. | n.d. | n.d. | 16.57 |
| CP2 Monomol. C1I | 97.51 | n.d. | n.d. | n.d. | 71.50 |
| CP2 NMF | 2.49 | n.d. | n.d. | n.d. | 28.5 |

TABLE 7

(liquid, 25° C.) - values given as [%]

|  | $t_0$ | 1 month |
|---|---|---|
| P1 Monomol. C1I | 99.55 | 97.36 |
| P1 NMF | 0.45 | 2.64 |
| P2 Monomol. C1I | 99.55 | 97.83 |
| P2 NMF | 0.45 | 2.17 |

TABLE 8

Bioavailability of C1-Ihnibitor of subcutaneously administered preparations compared to intravenously administered preparations of the same dose.

|  | Applied dose [IU/kg] | % AUC of i.v. |
|---|---|---|
| P2 i.v. | 40 | 100 |
| P2 s.c. | 40 | 72 |
| P2 i.v. | 70 | 100 |
| P2 s.c. | 70 | 75 |
| P3 i.v. | 40 | 100 |
| P3 s.c. | 40 | 95 |

REFERENCES

Kumar et al. C1-Esterase Inhibitor from Human Plasma—An Improved Process to Achieve Therapeutic Grade Purity; J. BIOPROCESS BIOTECH. 2014; 4 (6):174

Sim and Reboul. Preparation and Properties of Human C1 Inhibitor; METHODS IN ENZYMOLOGY. 1981; Vol. 80:43-54

Prograis et al. Purification of C1 Inhibitor; JOURNAL OF IMMUNOLOGICAL METHODS. 1987; Vol. 99:113-122

Teh and Froger. Evaluation of the chromatographie procedure for the preparation of a high-purity C1-esterase inhibitor concentrate from cryosupernatant plasma; JOURNAL OF CHROMATOGRAPHY. 1992; Vol. 582: 65-70

Feussner et al. Biochemical comparison of four commercially available C1 esterase inhibitor concentrates for treatment of hereditary angioedema; TRANSFUSION. 2014; 54:2566-2573

The invention claimed is:

1. A C1-esterase-inhibitor (C1-Inh) preparation, wherein the C1-Inh preparation comprises histidine in a concentration range of 5 to 400 mM but does not comprise citrate or phosphate, wherein the C1-Inh is in a concentration of 150 to 1000 IU/ml, and wherein the C1-Inh preparation further comprises one or more additional natural amino acids, selected from arginine and glycine.

2. The C1-Inh preparation of claim 1, wherein the histidine is in a concentration range of 8 to 300 mM.

3. The C1-Inh preparation of claim 1, wherein the C1-Inh preparation is suitable for subcutaneous or intravenous application.

4. The C1-Inh preparation of claim 1, wherein the natural amino acid is arginine present in a concentration range of 10 to 300 mM.

5. The C1-Inh preparation of claim 4, further comprising the natural amino acid glycine in a concentration range of 5 to 200 mM.

6. The C1-Inh preparation of claim 1, further comprising a salt, wherein the salt is sodium chloride in a concentration range of 8 to 150 mM.

7. The C1-Inh preparation of claim 1, wherein pH of the preparation is in a range of 6.0 to 8.0.

8. The C1-Inh preparation of claim 1, wherein osmolality of the C1-Inh preparation is in a range of 200 to 800 mOsmol/kg.

9. The C1-Inh preparation of claim 1, wherein total concentration of amino acids in the C1-Inh preparation is in a range of 50 to 600 mM.

10. The C1-Inh preparation of claim 1, wherein the C1-Inh preparation is lyophilized.

11. The C1-Inh preparation of claim 10, wherein preparation further comprises sodium chloride and arginine, and wherein the preparation after reconstitution has an osmolality of 200-800 mOsmol/kg and a pH value of 6.0 to 8.0.

12. The C1-Inh preparation of claim 11, wherein the preparation after reconstitution comprises 10-100 mM sodium chloride, 5-400 mM histidine and 5-400 mM arginine.

13. The C1-Inh preparation of claim 11, wherein the preparation after reconstitution comprises 25-35 mM sodium chloride, 10-20 mM histidine and 70-90 mM arginine, and wherein the preparation after reconstitution has an osmolality of 200-800 mOsmol/kg and a pH value of 7.1 to 7.5.

14. The C1-Inh preparation of claim 11, wherein the preparation after reconstitution comprises 25-35 mM sodium chloride, 20-40 mM histidine and 90-115 mM arginine, and wherein the preparation after reconstitution has an osmolality of 200-800 mOsmol/kg and a pH value of 7.1 to 7.5.

15. The C1-Inh preparation of claim 11, wherein the preparation after reconstitution comprises 25-40 mM sodium chloride, 100-140 mM histidine, 90-130 mM arginine and 5-30 mM glycine, and wherein the preparation after reconstitution has an osmolality of 380-500 mOsmol/kg and a pH value of 7.1 to 7.5.

16. The C1-Inh preparation of claim 10, wherein the preparation after reconstitution has a bioavailability of subcutaneously applied C1-Inh of more than 60% of an intravenously applied C1-Inh administered at the same dose, determined as area under the curve (AUC) over 168 hours.

17. The C1-Inh preparation of claim 11, wherein the preparation has a stability of at least 24 months when being stored at 1° C. to 35° C.

18. The C1-Inh preparation of claim 1, wherein the preparation is liquid.

19. The C1-Inh preparation of claim 18, further comprising sodium chloride and arginine, wherein the preparation has an osmolality of 200-800 mOsmol/kg and a pH value of 6.0 to 8.0.

20. The C1-Inh preparation of claim 19, comprising 10-100 mM sodium chloride, 5-400 mM histidine and 5-400 mM arginine, wherein the preparation has an osmolality of 200-800 mOsmol/kg and a pH value of 7.1 to 7.5.

21. The C1-Inh preparation of claim 19, comprising 10-100 mM sodium chloride, 10-100 mM histidine and 30-200 mM arginine, wherein the preparation has an osmolality of 200-800 mOsmol/kg and a pH value of 6.0 to 8.0.

22. The C1-Inh preparation of claim 19, comprising 25-35 mM sodium chloride, 100-140 mM histidine, 90-130 mM arginine and 5-30 mM glycine, wherein the preparation has an osmolality of 380-500 mOsmol/kg and a pH value of 7.1 to 7.5.

23. The C1-Inh preparation of claim 19, comprising of 25-35 mM sodium chloride, 20-40 mM histidine and 90-115 mM arginine, wherein the preparation has an osmolality of 200-350 mOsmol/kg and a pH value of 7.1 to 7.5.

24. The C1-Inh preparation of claim 19, comprising of 25-35 mM sodium chloride, 10-20 mM histidine, 70-90 mM arginine, and further comprising 35-65 mM glycine, wherein the preparation has an osmolality of 200-350 mOsmol/kg and a pH value of 7.1 to 7.5.

25. The C1-Inh preparation of claim 19, wherein the preparation has a stability of at least 12 months at 1° ° C. to 8° C.

26. The C1-Inh preparation of claim 18, wherein the preparation has a bioavailability of subcutaneously applied C1-Inh of more than 60% of an intravenously applied C1-Inh administered at the same dose, determined as AUC over 168 hours.

* * * * *